United States Patent [19]

Zoltan et al.

[11] 4,312,835
[45] Jan. 26, 1982

[54] THERMAL CONTROL MEANS FOR LIQUID CHROMATOGRAPH SAMPLES

[75] Inventors: Bart J. Zoltan, Old Tappan, N.J.; Richard A. Leese, Monsey, N.Y.

[73] Assignee: American Cyanamid Company, Stamford, Conn.

[21] Appl. No.: 141,758

[22] Filed: Apr. 21, 1980

[51] Int. Cl.³ .................. G01N 1/14; G01N 1/10; G01N 35/02
[52] U.S. Cl. .................. 422/70; 73/61.1 C; 219/415; 219/441; 219/433; 219/521; 422/102; 422/104
[58] Field of Search .................. 422/104, 102, 99, 73, 422/70; 219/295, 301, 328, 378, 441, 415, 433, 521, 533; 73/61.1 C

[56] References Cited

U.S. PATENT DOCUMENTS

| | | | |
|---|---|---|---|
| 3,271,112 | 9/1966 | Williams et al. | 422/73 |
| 3,607,099 | 9/1971 | Scordata et al. | 23/230 B |
| 3,918,913 | 11/1975 | Stevenson et al. | 73/425.6 |
| 3,932,067 | 1/1976 | Ball et al. | 447/339 |
| 3,975,946 | 8/1976 | Ball et al. | 73/61.1 C |
| 4,059,009 | 11/1977 | Ball et al. | 73/61.1 C |
| 4,131,547 | 12/1978 | Michel et al. | 210/198 C |

OTHER PUBLICATIONS

Kallen, Handbook of Instrumentation and Controls, McGraw-Hill, N.Y., N.Y., 1961, pp. 4-31.
Hackhs Chemical Dictionary, McGraw-Hill, 1969, p. 494.

Primary Examiner—Ronald Serwin
Attorney, Agent, or Firm—Robert P. Raymond

[57] ABSTRACT

A Peltier effect thermal control sample containment means for an automatic sample holding apparatus used in conjunction with a liquid chromatograph analysis. The apparatus provides for the cooling or heating of a plurality of liquid chromatography samples and the maintenance of said samples at specific temperatures for extended periods of time.

2 Claims, 2 Drawing Figures

THERMAL CONTROL MEANS FOR LIQUID CHROMATOGRAPH SAMPLES

FIELD OF THE INVENTION

This invention comprises a Peltier effect thermal control sample containment means for an automatic samples holding apparatus used in conjunction with a liquid chromatographic analysis. The apparatus provides for the cooling or heating of a plurality of liquid chromatography samples and the maintenance of said samples at specific temperatures for extended periods of time.

BACKGROUND OF THE INVENTION

The present invention is concerned with the problem of temperature control of samples and the sample containment platform means which, in the preferred embodiment, is adapted to an automatic sample injector (particularly Micromeritics Instrument Corporation, Model 725) or other similar device. U.S. Pat. No. 3,607,099 to Scordato et al., concerns sample temperature control. The invention of the instant application solves some of the problems of the previous technology. The function of a temperature controlled sample containment platform means is to uniformly maintain the plurality of sample solutions at specific predetermined temperatures for whatever period of time is required for holding said samples prior to the completion of chromatographic analysis of said samples. This is useful and required if a sample is labile and degrades at room temperature. In the performance of automated chromatographic analytical procedures the sample solution resides in the sample holding means for an extended period of time awaiting analysis. In certain cases, such as in the analysis of antibiotics, it is important that the samples be maintained at a specific temperature considerably below ambient temperature to lessen the likelihood and level of sample degradation during this waiting period. Similarly labile material such as vaccines or genetic materials or hormones may degrade at room temperature. Additionally, in cases in which volatile material such as hexane or ether are used as sample solvents or diluents, cooling the sample by the means of the present invention would limit the loss of solvent due to evaporation. Elevated temperatures are required where analysis at a constant temperature which is above ambient is required. The state of the art does not provide for fully effective heating/cooling devices employing the use of the Peltier element for chromatographic analysis sample holder means. Peltier elements will be considered here to have an active surface, the surface where the desired heating or cooling is effected, and a reactor surface of converse temperature change.

It is an object of the present invention to provide a thermal control means providing for the cooling or heating of from one to a plurality of samples for liquid chromatographic analysis to a specific temperature for an extended period of time.

SUMMARY

The thermal control means for liquid chromatography samples of this invention which comprises from one to a plurality of Peltier elements, is characterized by three critical factors; (1) intimate contact between active surface of the Peltier element and the element to be temperature controlled, here the sample holding body; (2) intimate contact between the reactive surface of the Peltier element and a heat sink; and (3) insulation between the sample holding portion of the apparatus whose temperature is to be altered by said active surface and the heat sink portion. These are critical in view of the limited capacity of a Peltier element to effect heating or cooling of an active surface without offsetting transmission from the reactive surface. Peltier elements at a distance from the sample holder body would not be effective.

DETAILED DESCRIPTION OF THE INVENTION

This invention will be better understood with reference to the following detailed description of the figures; such description is merely illustrative of the invention. The invention will be limited only by the claims. Other embodiments of the invention will be immediately obvious to those skilled in the art without departing from the spirit of the invention.

Figure 2:
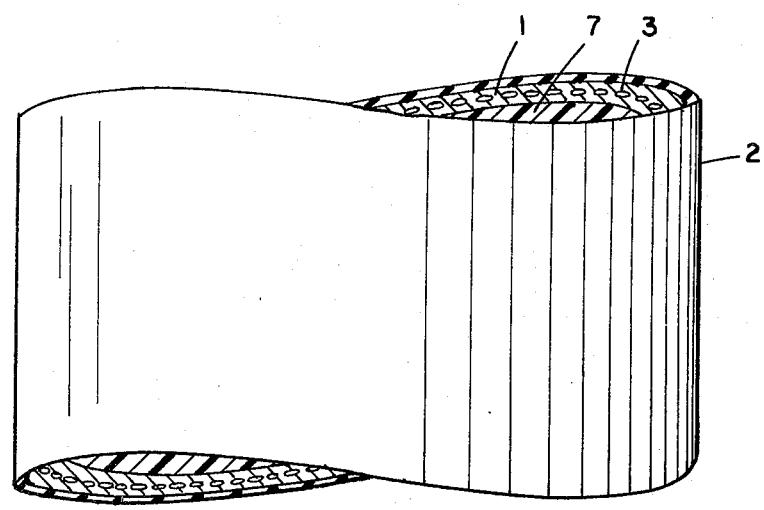
FIG. 2 is a side view of the sample holder (1) and elements (2), (3) and (7) described below.
Figure 1:
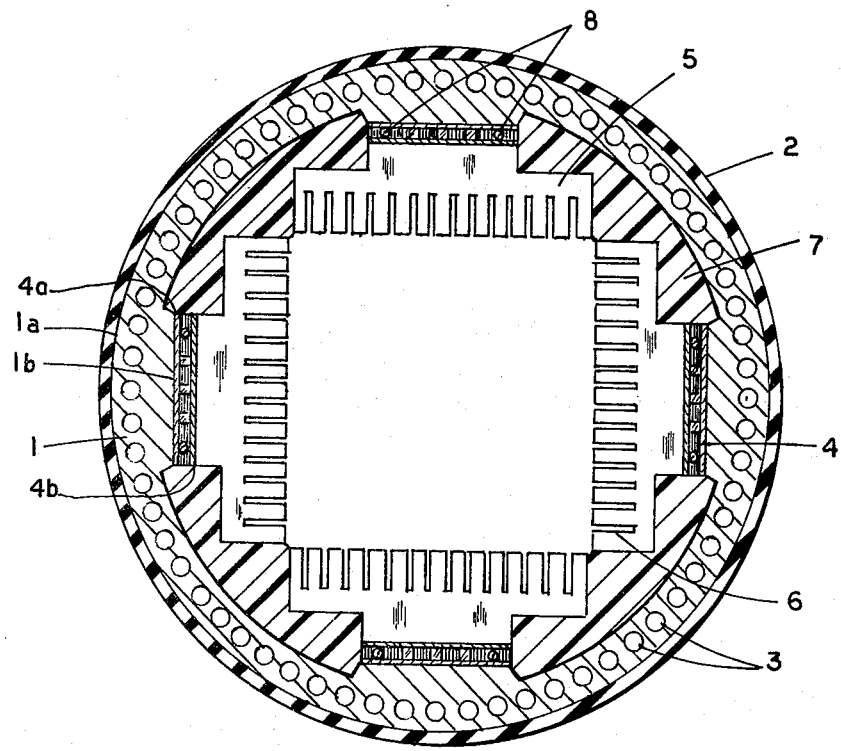
FIG. 1 is a top view of the thermal control device of this invention.

FIG. 1 shows a sample holder body (1) with an inner (1b) and outer surface (1a), said sample holder body being formed of a heat conductive material such as a metal and preferably aluminum or copper or the like. In said sample holder body are sample containment positions (3). Surrounding the outer surface of the sample holder body is insulating material (2). The sample holder body inner surface (1b) is characterized by a configuration suitable for intimate contact with an active surface of a Peltier element (4) wherein said Peltier element bears an active surface (4a) and a reactive surface (4b) and sample holder body inner surface (1b) is in intimate contact with the Peltier element active surface (4a).

In intimate contact with the Peltier element reactive surface (4b) is heat exchange means (5) and such heat exchange means (5) continuing as a heat dissipation means (6), here cooling fins, though fluid cooling or fan cooling of cooling fins or other such means annexed to the heat exchange meams would also serve as a heat dissipating means. For effective temperature control of the samples, insulating material (7) separating sample holder body (1) and heat exchange means (5) is a critical element preventing the temperature-altered sample holder body from exchanging heat with the heat exchange means. Electric power supply points of connection to said Peltier element are shown as (8).

From the above description it will be understood by those skilled in the art that in the present application the active surface of the Peltier device will be driven in such a manner that it will be heated or cooled when the samples are desired to be heated or cooled. A concomitant of which is that when the active surface of the Peltier device is for example cooled, the reactive surface temperature becomes elevated relative to ambient temperature. In view of the limited efficiency of the Peltier device, the extensive heat dissipation through element (6) is required. Backflow of heat would offset the heating/cooling effect of the active surface of the Peltier device without the insulating material of (7). This is a critical element of the instant device for effective temperature control of the samples. Furthermore, locating the Peltier device at a distance from the sample holder body (1) to be cooled would be an ineffective embodiment of this invention. This is particularly so in that a preferred embodiment requires reduction of sample temperature from ambient, about 20°–25° C., to maintenance of sample temperature at about 0°–4° C.

We claim:

1. In a liquid chromatographic sampling device having an automatic sample injector, the improvement comprising a thermal control sample containment means comprising:
   (a) sample holder body of a heat conductive material having from one to a plurality of sample contaimment means and from one to a plurality of
   (b) Peltier devices, said devices each having an active surface and a reactive surface and said sample holder body being in intimate contact with the active surface of each Peltier device adapted to provide cooling or heating of the samples being chromatographed and
   (c) insulation between said sample holder body and said reactive surface of each Peltier device and each said reactive surface of each said Peltier device being in intimate contact with
   (d) a heat exchange means.

2. In a liquid chromatography sampling device having an automatic sample injector, the improvement comprising a thermal control sample containment means capable of reducing sample temperature from about 20°–25° C. to about 0°–4° C. comprising:
   (a) sample holder body of a heat conductive material having from one to a plurality of sample containment means and from one to a plurality of
   (b) Peltier devices, said devices each having an active surface and a reactive surface and said sample holder body being in intimate contact with the active surface of each Peltier device adapted to provide cooling of the samples being chromatographed and
   (c) insulation between said sample holder body and said reactive surface of each Peltier device and each said reactive surface of each said Peltier device being in intimate contact with
   (d) a heat exchange means.

* * * * *